(12) United States Patent
Panotopoulos

(10) Patent No.: US 7,625,763 B2
(45) Date of Patent: Dec. 1, 2009

(54) RAPID DIAGNOSTIC TEST SYSTEMS AND METHODS

(75) Inventor: George Panotopoulos, Santa Clara, CA (US)

(73) Assignee: Alverix, Inc., San Jose, CA (US)

( * ) Notice: Subject to any disclaimer, the term of this patent is extended or adjusted under 35 U.S.C. 154(b) by 379 days.

(21) Appl. No.: 11/518,782

(22) Filed: Sep. 11, 2006

(65) Prior Publication Data

US 2008/0064119 A1 Mar. 13, 2008

(51) Int. Cl.
*G01N 33/558* (2006.01)
(52) U.S. Cl. .......................... 436/514; 422/56; 422/57; 422/58; 435/287.2; 435/287.7; 435/287.9; 435/805; 435/810; 435/970; 436/169; 436/518; 436/530; 436/810
(58) Field of Classification Search ........................ None
See application file for complete search history.

(56) References Cited

U.S. PATENT DOCUMENTS 6,924,153 B1 * 8/2005 Boehringer et al. ......... 436/514
7,144,742 B2 * 12/2006 Boehringer et al. ......... 436/514

OTHER PUBLICATIONS

Lou et al, "One-Step Competitive Immunochromatographic Assay for Semiquantitative Determination of Lipoprotein(a) in Plasma", Clin. Chem. 39/4, 619-624, (1993).*

* cited by examiner

*Primary Examiner*—Christopher L Chin
(74) *Attorney, Agent, or Firm*—K&L Gates LLP

(57) ABSTRACT

A rapid diagnostic test system includes a lateral-flow strip for performing a binding assay. The lateral-flow strip contains a binding agent having a deposition density that varies periodically along at least a portion of the lateral-flow strip. The test system further includes an imaging system that is used to capture an image of the portion of the lateral-flow strip.

20 Claims, 16 Drawing Sheets

RAPID DIAGNOSTIC TEST SYSTEMS AND METHODS

DESCRIPTION OF THE RELATED ART

Rapid diagnostic test systems are often used as a convenient tool for detecting various substances that may be present in items such as blood, urine, and water. In one such test system, a lateral-flow strip is used for performing a binding assay, which, in layman's terms, can be best illustrated by a well known application—a pregnancy test using a pregnancy test strip. As is known, a pregnancy test strip can be used to rapidly test a woman's urine for the presence of certain substances indicative of a pregnancy. The test includes depositing a urine sample on the test strip and visually inspecting a portion of the strip for a change in color. Unfortunately, various users may find that the change in color is not distinct enough to be recognizable in a consistent and unambiguous manner.

In another well known application, a test strip is used for drug testing. The presence of the drug is indicated by a change in color of a portion of the test strip. Here again, the change in color cannot be consistently and unambiguously identified by all users. Furthermore, even if a change in color is recognizable, the test does not provide a quantitative measure of the drug.

Based on the above-mentioned handicaps, an unaddressed need exists in the industry to overcome such deficiencies and inadequacies.

SUMMARY

A rapid diagnostic test system includes a lateral-flow strip for performing a binding assay. The lateral-flow strip contains a binding agent having a deposition density that varies periodically along at least a portion of the lateral-flow strip. The test system further includes an imaging system that is used to capture an image of the portion of the lateral-flow strip.

BRIEF DESCRIPTION OF THE DRAWINGS

Many aspects of the invention can be better understood with reference to the following drawings. The components in the drawings are not necessarily to scale. Instead, emphasis is placed upon clearly illustrating the principles of the invention. Moreover, in the drawings, like reference numerals designate corresponding parts throughout the several views.

DETAILED DESCRIPTION

The rapid diagnostic test system in accordance with the invention includes a lateral-flow strip and an imaging system. The lateral-flow strip contains a binding agent having a deposition density that varies in a periodic pattern. The imaging system is used to capture an image of at least a portion of the lateral-flow strip after a sample has been deposited upon the lateral-flow strip. In one exemplary embodiment, the captured image is analyzed by an image data analyzer that uses the periodic pattern to generate qualitative and/or quantitative test results. While a gross change in color provides a "pass-fail" type of test result, the magnitude of the change in color of the periodic pattern provides a quantitative result of the diagnostic test. In an alternative embodiment, the captured image is visually inspected by a human operator to detect a change in color of the periodic pattern.

Various embodiments of the rapid diagnostic test system as well as various methods of rapid diagnostic testing in accordance with the invention are described below in further detail.

Figure 1:
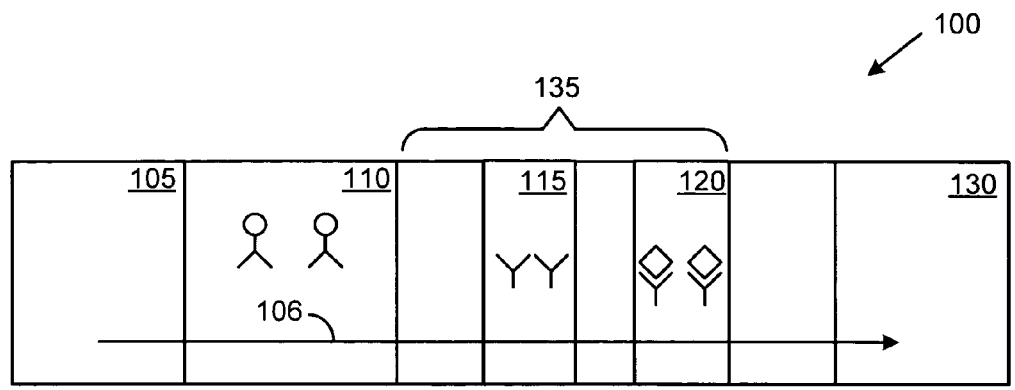
FIG. 1 shows a symbolic representation of the contents of an exemplary lateral-flow strip in accordance with the invention, prior to its use in a test process.

FIG. 1 shows a symbolic representation of the contents of an exemplary lateral-flow strip 100 in accordance with the invention, prior to its use in a test process. Various portions of lateral-flow strip 100 are specifically configured to carry out certain operations upon a test sample. These portions, which are generally referred to herein as regions, are attached to a common backing (not shown) of a material such as chemically treated nitrocellulose that allows fluid flow by capillary action through the various regions.

Typically, a test sample such as blood, urine, saliva, or other solution is deposited on a deposition region 105 and flows through, via capillary action along the path indicated by arrow 106, to a collection region 130. Adjacent to deposition region 105 is a label zone 110 containing labeled antibodies for indirect labeling of a target analyte that may be present in the test sample. One example of a labeled antibody, used in medical testing, is an immunoglobulin with attached dye molecules.

Next to label region 110 is a detection region 135 containing a test result region 115 and a test completion region 120. Test result region 115 contains a binding agent capable of specifically binding the labeled target analyte. When the target analyte is present in the test sample, test result region 115 changes color typically within a matter of minutes from the commencement of the test. Test completion region 120, which is downstream to test result region 115, is useful for indicating that the test sample has flowed through lateral-flow strip 100, specifically through test result region 115. This is carried out by binding and retaining the labeled antibodies in the test completion region 120, which consistently results in a visible change in color of test completion region 120, irrespective of a change in color of test result region 115. Beyond test completion region is collection region 130 wherein any residual test sample is collected.

Figure 2:
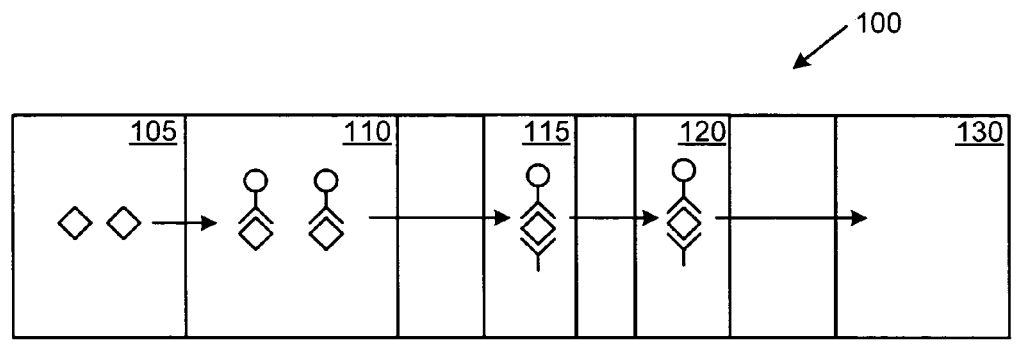
FIG. 2 shows a symbolic representation of a test process wherein a sample flows across the lateral-flow strip of FIG. 1 to produce a positive test result.

FIG. 2 shows a symbolic representation of a test process when the test sample contains a target analyte. The target analyte flows from deposition region 105 into label region 110, where labeled antibodies indirectly label the target analyte. The labeled target analyte then flows into test result region 115 where the labeled target analyte attaches to a binding agent thereby resulting in a visible change in color of test result region 115. The test sample continues to flow through to test completion region 120, which also changes color to indicate completion of the test, and from there any residual test sample is collected in collection region 130.

Figure 3:
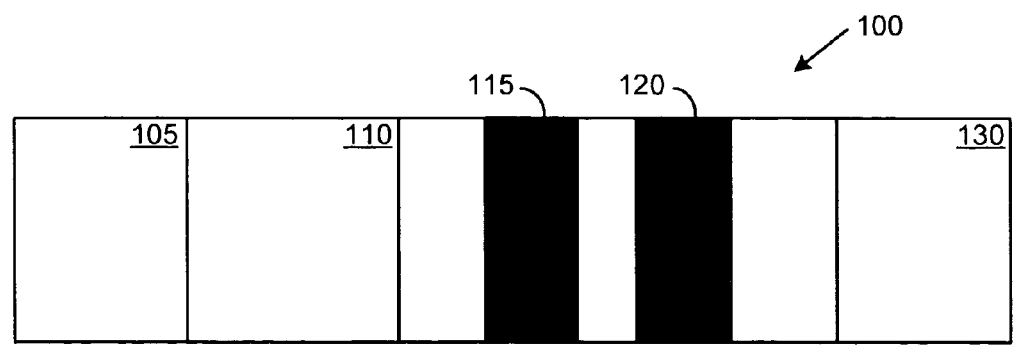
FIG. 3 shows a visual representation of the positive test result obtained in the test process of FIG. 2.

FIG. 3 shows a visual representation of the test result obtained in the test process described above. In this case, both test result region 115 and test completion region 120 have visibly changed color thereby indicating a positive test result.

Figure 4:
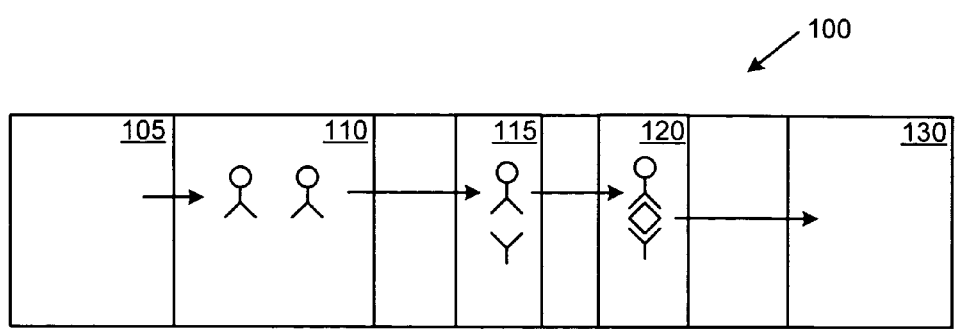
FIG. 4 shows a symbolic representation of a test process wherein a sample flows across the lateral-flow strip of FIG. 1 to produce a negative test result.
Figure 5:
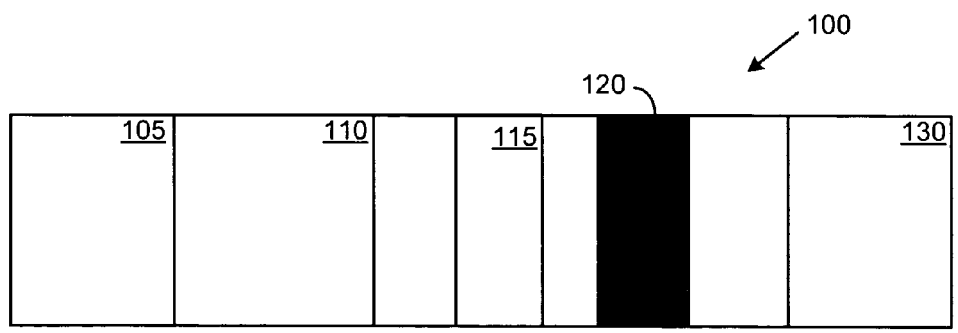
FIG. 5 shows a visual representation of the negative test result obtained in the test process of FIG. 2.

FIG. 4 shows a symbolic representation of a test process when the test sample does not contain a target analyte. In contrast to FIG. 2, test result region 115 does not contain labeled target analytes attached to the binding agent. Consequently, FIG. 5, which shows a visual representation of the test result, shows no coloring in test result region 115. However, test completion region 120 has visibly changed color to indicate completion of the test. The color combination provided in this case by test result region 115 and test completion region 120 is indicative of a negative test result.

Figure 6:
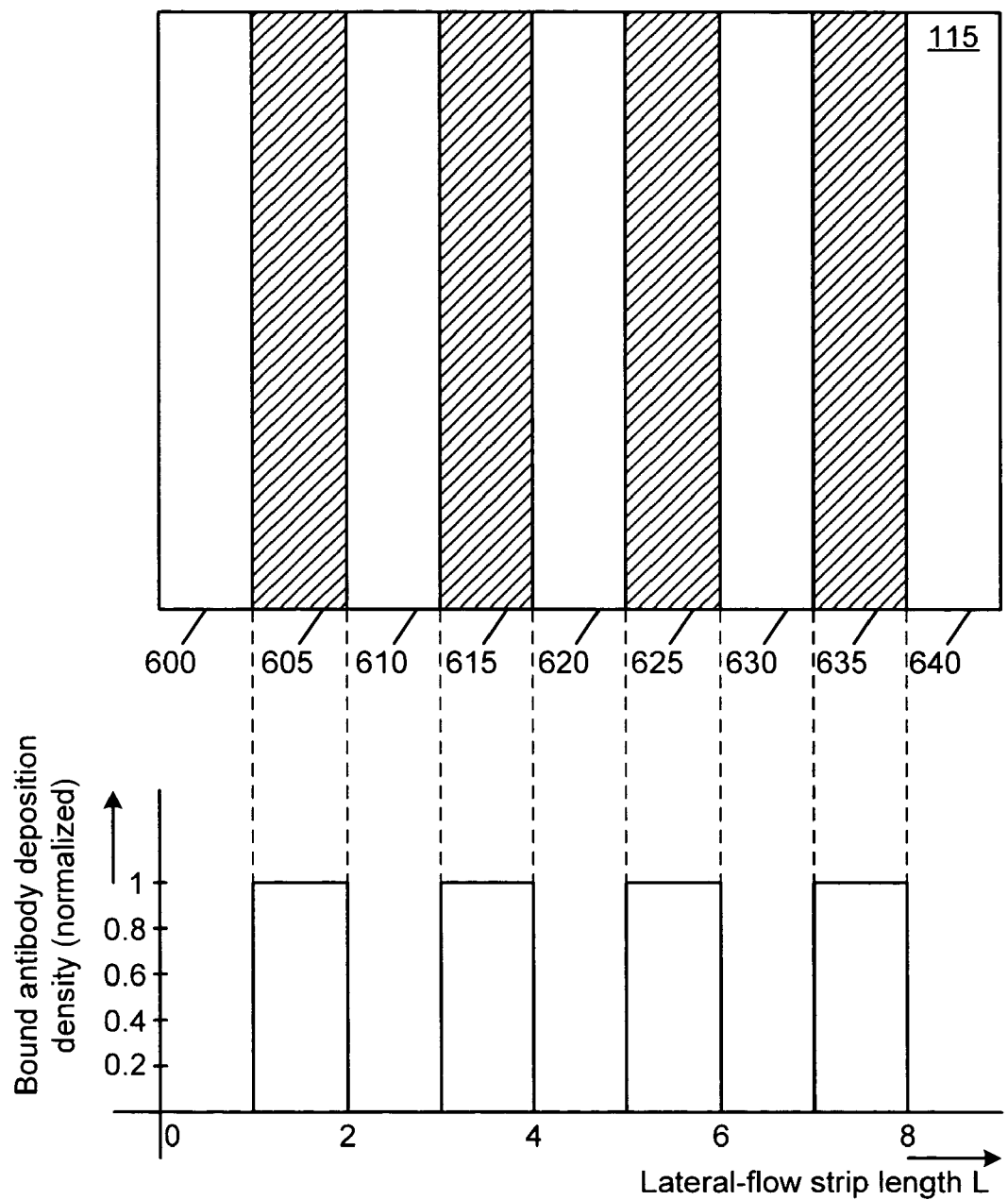
FIG. 6 shows a first exemplary embodiment in accordance with the invention, of a test result region of the lateral-flow strip of FIG. 1.

FIG. 6 shows a first exemplary embodiment in accordance with the invention, of test result region 115 of lateral-flow strip 100, where test result region 115 contains a binding agent having a deposition density that varies in a periodic pattern. In this exemplary embodiment, the periodic pattern is a binary pattern as indicated by the graph of deposition density versus length L of lateral-flow strip 100. Specifically, a first group of regions (regions 605, 615, 625 and 635) contains the binding agent, while a second group of regions (regions 600, 610, 620, 630 and 640) does not contain the binding agent. Each of the regions of the first group is interspersed with each of the regions of the second group. Thereby, the regions are arranged in the following pattern: 600-605-610-615-620-625-630-635-640. As a result of this arrangement, the deposition density of the binding agent constitutes a periodic pattern, specifically, in this example, a binary "1-0" pattern.

Figure 7:
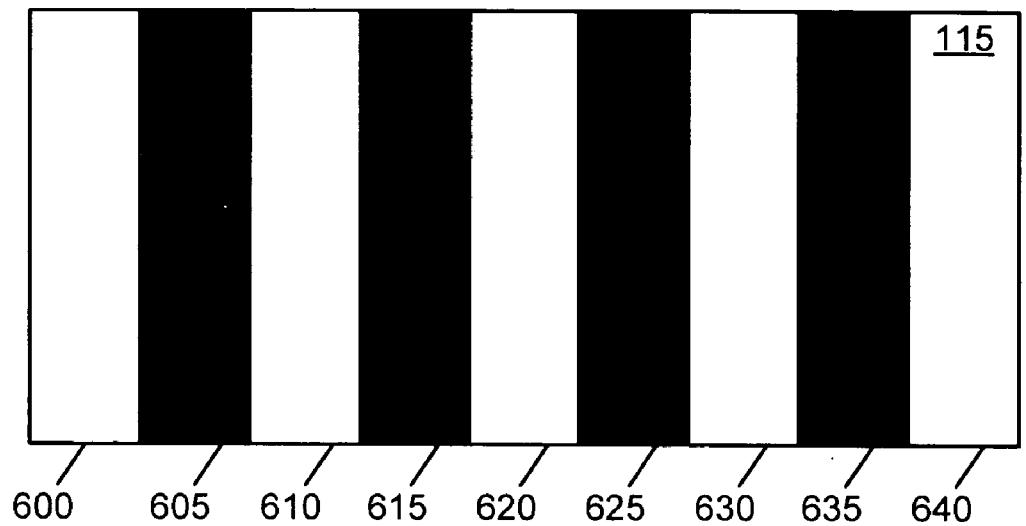
FIG. 7 shows a positive test result displayed on the test result region of FIG. 6.

FIG. 7 shows a positive test result displayed on test result region 115 of the embodiment described above using FIG. 6. The first group of regions (regions 605, 615, 625 and 635) has changed color because the target analyte was present in the test sample. The second group of regions (regions 600, 610, 620, 630 and 640), which does not have the binding agent, remains unaffected. The change in color of the first group is clearly visible as a periodic binary pattern in lateral-flow strip 100.

Figure 8:
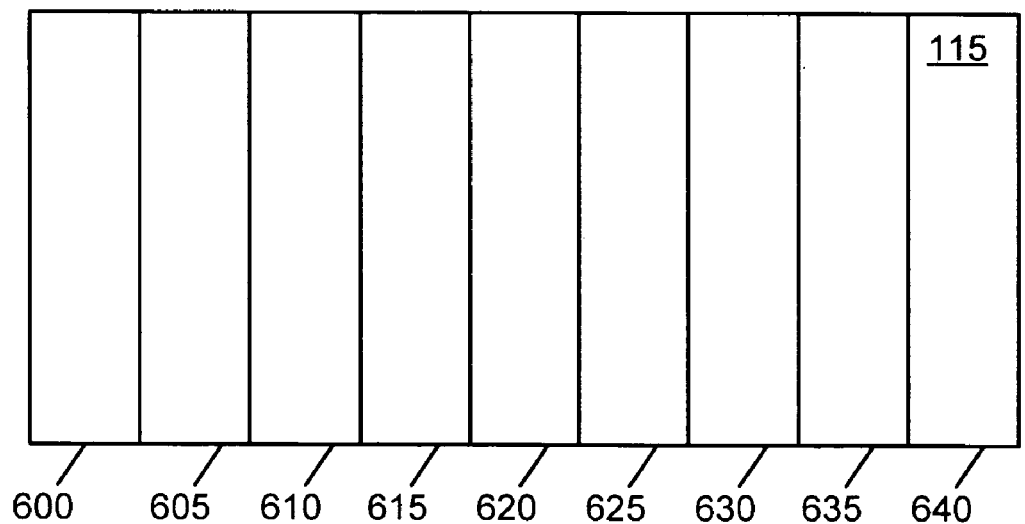
FIG. 8 shows a negative test result displayed on the test result region of FIG. 6.

FIG. 8 shows a negative test result displayed on test result region 115 of the embodiment described above using FIG. 6. The first group of regions (regions 605, 615, 625 and 635), which has the binding agent, remains unchanged in color because the target analyte was not present in the test sample. The second group of regions (regions 600, 610, 620, 630 and 640), which does not have the binding agent, remains unaffected.

Figure 9:
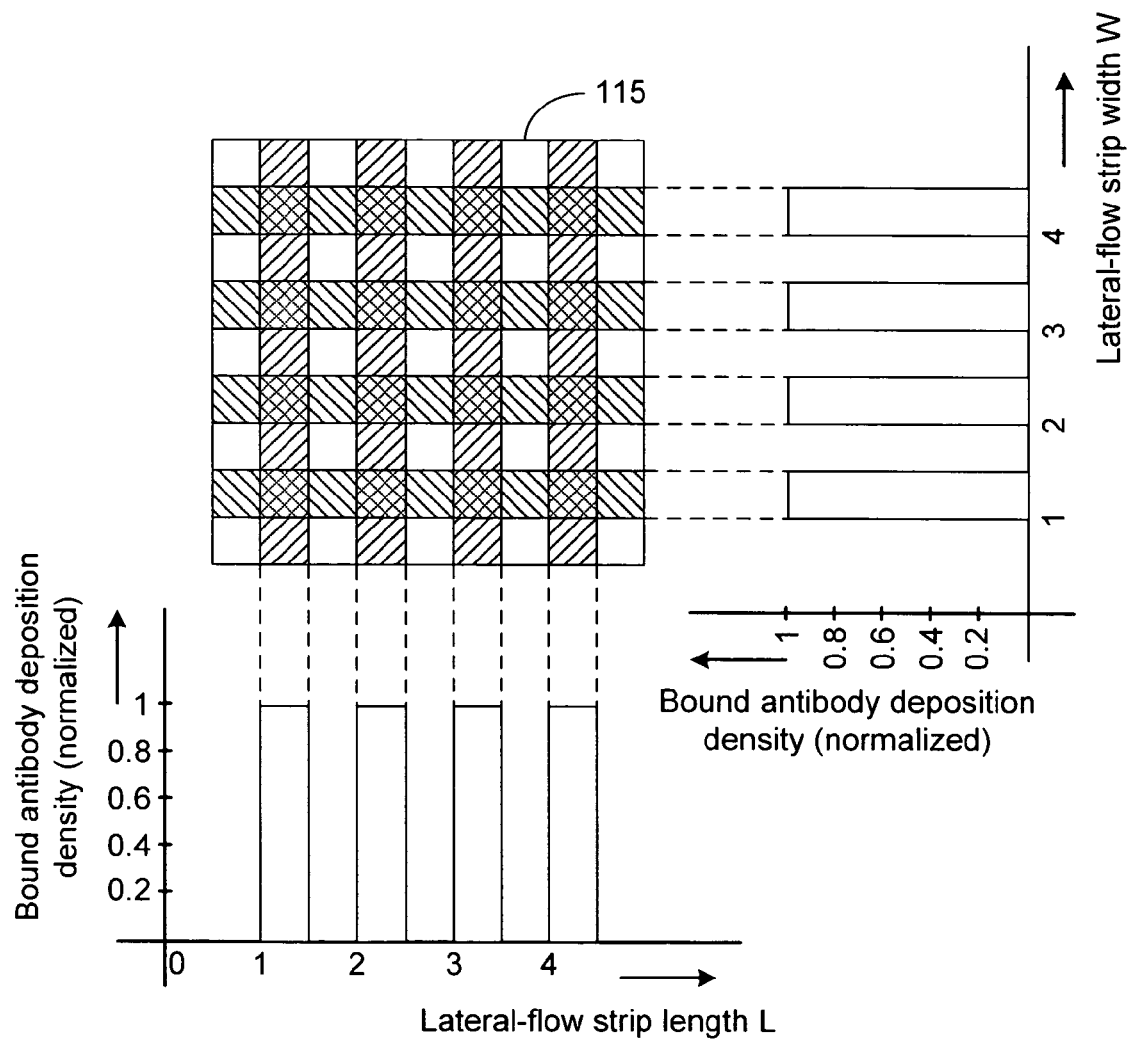
FIG. 9 shows a second exemplary embodiment in accordance with the invention, of the test result region of the lateral-flow strip of FIG. 1.

FIG. 9 shows a second exemplary embodiment in accordance with the invention of lateral-flow strip 100 where test result region 115 contains a binding agent having a deposition density that varies in a 2-dimensional periodic pattern. In this example, the 2-dimensional periodic pattern is formed of a first periodic pattern oriented in one direction and a second periodic pattern oriented in a different direction. The first periodic pattern is a binary pattern as indicated by the graph of deposition density versus length L of lateral-flow strip 100. The second periodic pattern is also a binary pattern as indicated by the graph of deposition density versus width W of lateral-flow strip 100.

In this exemplary embodiment, the first and second periodic patterns are orthogonal to one another and are similar (binary) to one another. The orthogonal orientation of the two periodic patterns results in an overall checkerboard pattern of light and dark areas of color density when the test is positive.

In other embodiments, the first and second periodic patterns may be oriented in various other individual directions. Additionally, each of the first and second periodic patterns may be different to one another. For example, the spatial frequency of the first periodic pattern may be different than the spatial frequency of the second periodic pattern. As a further example, the first periodic pattern may be a sinusoidal pattern while the second periodic pattern is a binary pattern.

Figure 10A:
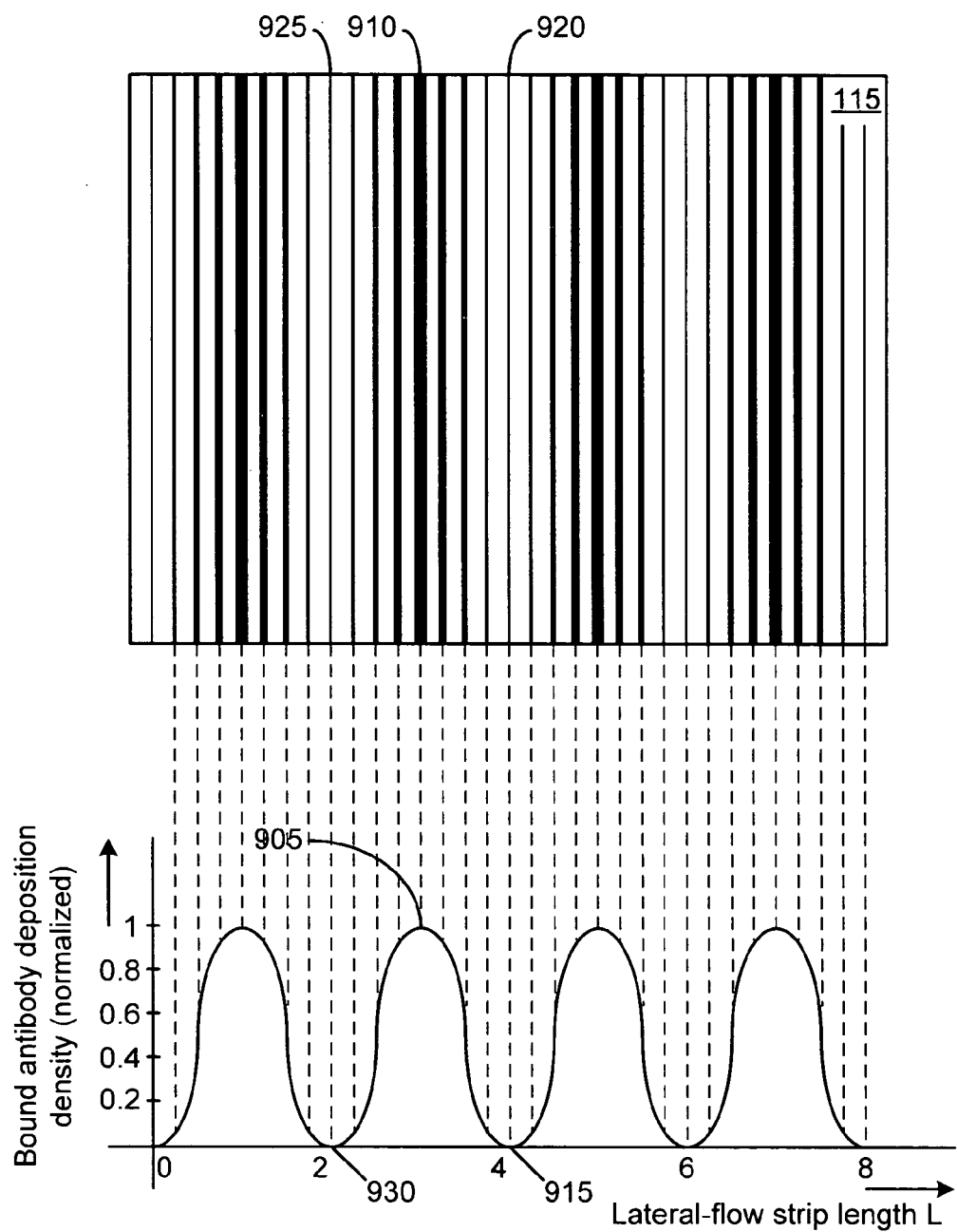
FIG. 10A shows a third exemplary embodiment in accordance with the invention, of the test result region of the lateral-flow strip of FIG. 1.

FIG. 10A shows a third exemplary embodiment in accordance with the invention of lateral-flow strip 100 where test result region 115 contains a binding agent having a deposition density that varies in a third exemplary periodic pattern. In this exemplary embodiment, the periodic pattern is a sinusoidal pattern as indicated by the graph of deposition density versus length L of lateral-flow strip 100. The peaks of the sinusoidal pattern coincide with areas of lateral-flow strip 100 where the deposition density of the binding agent is at a maximum, while the valleys of the sinusoidal pattern coincide with areas of lateral-flow strip 100 where the deposition density of the binding agent is at a minimum. The deposition density of the binding agent varies sinusoidally between the peaks and the valleys.

For example, sinusoidal point 905 coincides with area 910 of lateral-flow strip 100 where the deposition density of the binding agent is at a maximum, and sinusoidal points 930 and 915 coincide with areas 925 and 920 respectively of lateral-flow strip 100 where the deposition density of the binding agent is at a minimum.

Figure 10B:
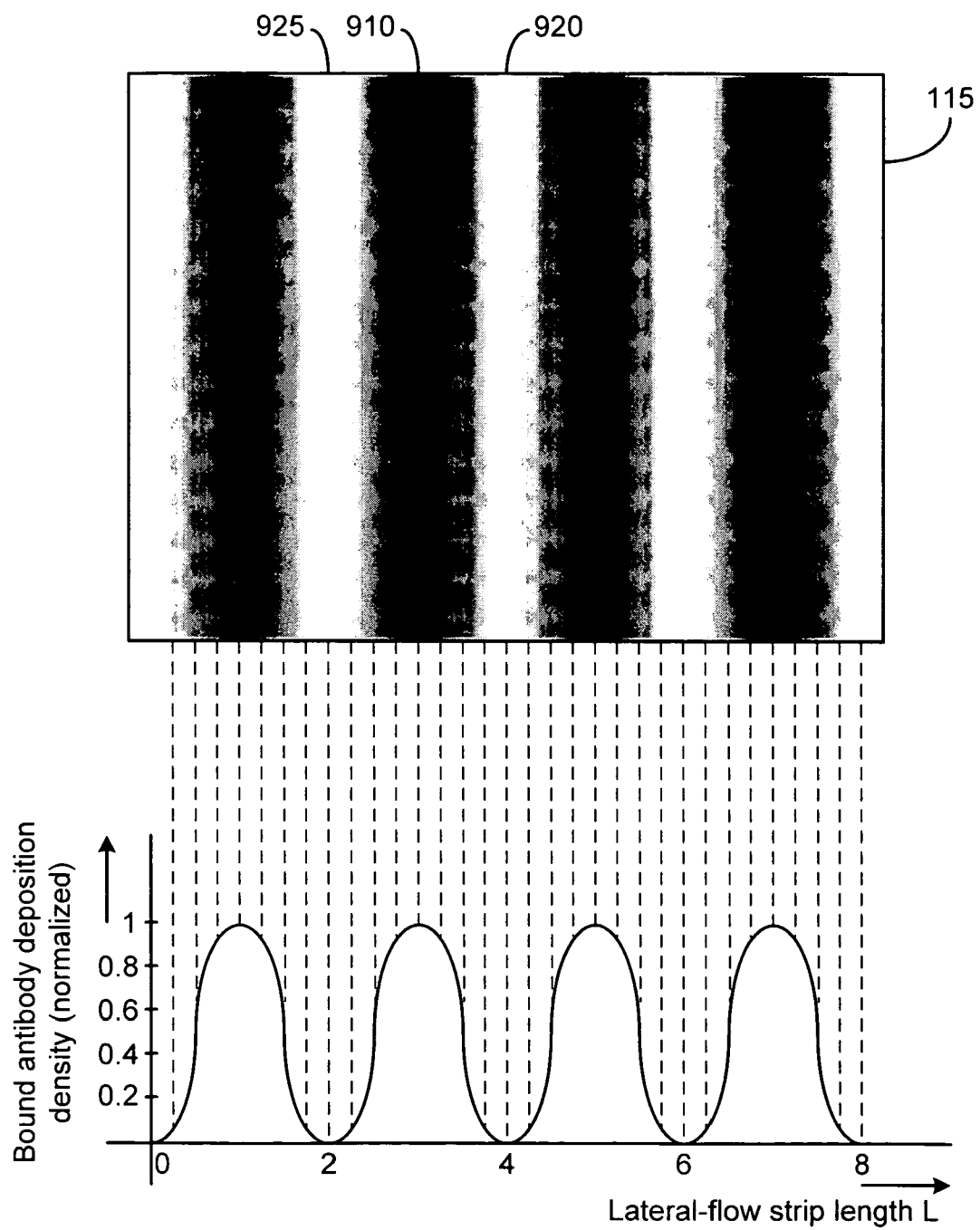
FIG. 10B shows further details of the test result region of FIG. 10A.

While FIG. 10A shows several discrete areas of varying deposition density along lateral-flow strip 100, it will be understood that this has been done merely for purposes of illustration, and a continuous, sinusoidal variation in deposition density exists between each of peak and adjacent valley. This aspect has been illustrated in FIG. 10B. When test result region 115 of lateral-flow strip 100 displays a positive result, the visible coloring has a maximum intensity at each of the peaks and a sinusoidal decrease in color intensity away from each peak. Consequently, in one exemplary embodiment, a positive test result is indicated by maximum color being visible in area 910 with a gradual reduction in color on either side of area 910, with no color being visible in areas 920 and 925. In another exemplary embodiment, a positive test result is indicated by maximum color in area 910 with a gradual reduction in color on either side of area 910, with very slight color being visible in areas 920 and 925.

Figure 11:
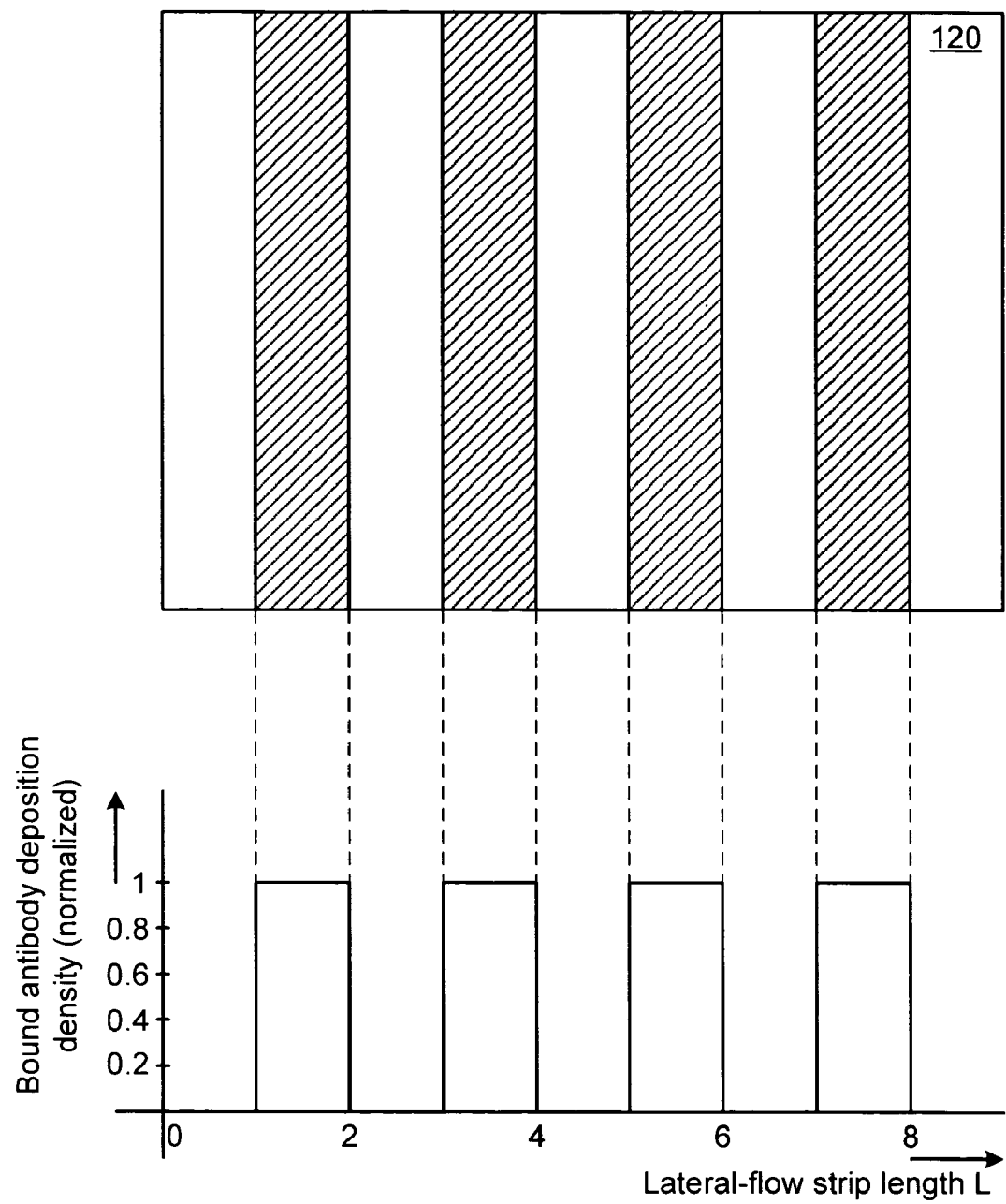
FIG. 11 shows a first exemplary embodiment in accordance with the invention, of a test completion region of the lateral-flow strip of FIG. 1.

While the description above has largely focused upon test result region 115, attention is now drawn to FIG. 11 which shows a first exemplary embodiment in accordance with the invention of test result completion region 120. Test result completion region 120 contains a binding agent having a deposition density that varies in a periodic pattern. In this example, the periodic pattern is a binary pattern. As mentioned above, a change in color of test completion region 120 indicates that a test sample has flowed across lateral-flow strip 100 and the test has been completed.

Figure 12:
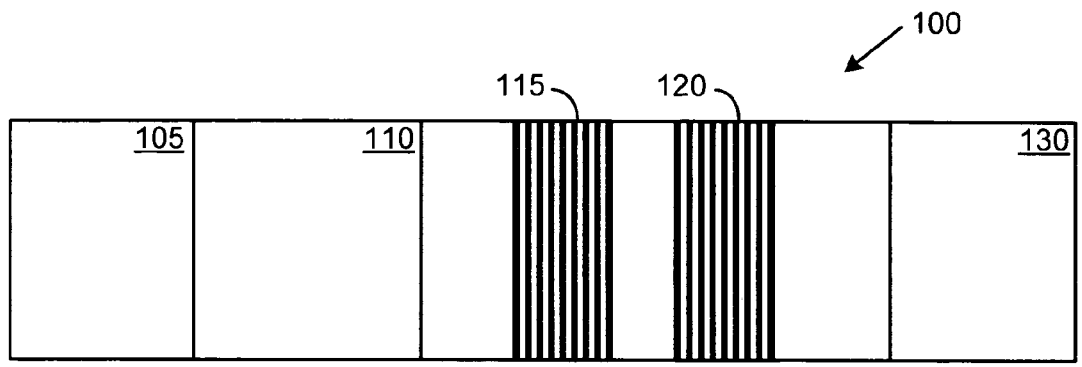
FIG. 12 shows a positive result on a lateral-flow strip containing the test completion region of FIG. 11.

FIG. 12 shows test completion region 120 when a test carried out upon lateral-flow strip 100 produces a positive test result. In this example, both test result region 115 and test completion region 120 contain a binding agent with a deposition density that varies in an exemplary binary pattern that is similar in both regions. Test result region 115 has changed color as a result of the positive test result. Test completion region 120 has also changed color to indicate completion of the test.

Figure 13:
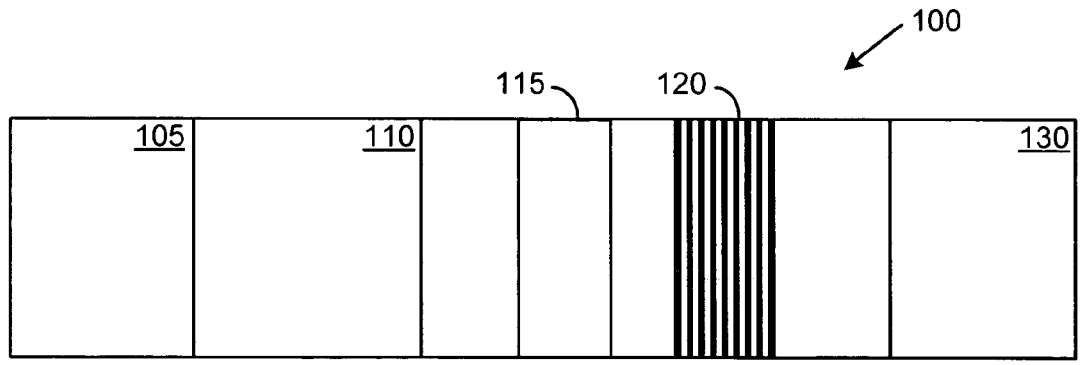
FIG. 13 shows a negative result on a lateral-flow strip containing the test completion region of FIG. 11.

FIG. 13 shows test completion region 120 when a test carried out upon lateral-flow strip 100 produces a negative test result. In this example, again, both test result region 115 and test completion region 120 contain a binding agent with a deposition density that varies in an exemplary binary pattern that is similar in both regions. Test result region 115 has not changed color because of the negative test result, while test completion region 120 has changed color to indicate completion of the test.

While the examples provided above refer to a visible change in color, it will be understood that in other embodiments in accordance with the invention, a test result is indicated by changes that are not necessarily visible to the human eye. As one among several alternative examples, a positive test result is indicated by a color change at an infra-red wavelength that is invisible to the human eye but is detectable by an instrument such as an infra-red camera. Invisible test results are advantageous for maintaining confidentiality, in drug testing, for example.

Figure 14:
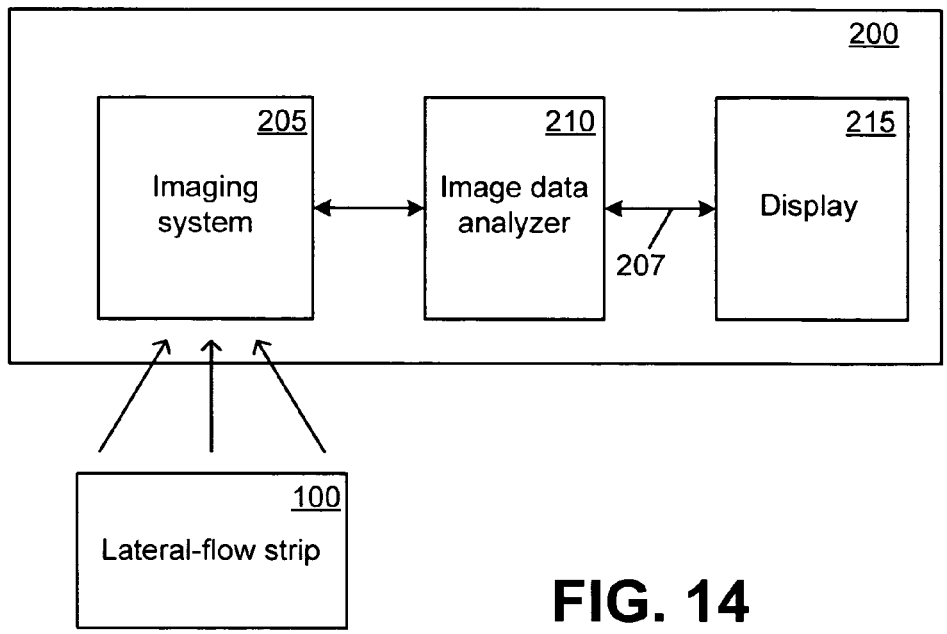
FIG. 14 shows a first exemplary embodiment in accordance with the invention, of a rapid diagnostic test system for obtaining test results from the lateral-flow strip of FIG. 1.

FIG. 14 shows a first exemplary embodiment in accordance with the invention, of a rapid diagnostic test system 200 for obtaining test results from the lateral-flow strip 100 described above. In one embodiment, rapid diagnostic test system 200 is a portable device, a hand-held unit for example. In another embodiment, rapid diagnostic test system 200 is a stationary device, such as a desktop unit.

Typically, rapid diagnostic test system 200 includes an imaging system 205, which is used to capture an image of at least a portion of lateral-flow strip 100. In one exemplary embodiment, imaging system 205 is a digital camera. The digital camera is operated to capture a partial or complete image of lateral-flow strip 100. A partial image includes test result region 115, and may optionally include test completion region 120 as well as other regions of lateral-flow strip 100. The captured image is available as digital image data that is provided by the digital camera to an image data analyzer 210. The digital image data is analyzed by image data analyzer 210, typically using digital image processing techniques, to identify the test result. A positive test result is produced when image data analyzer 210 detects the presence of the periodic pattern in test result region 115 of lateral-flow strip 100.

The periodic pattern present in test result region 115 is advantageously used as a priori information by image data analyzer 210 to generate test results. For example, a digital image processing technique of image data analyzer 210 uses the a priori periodic intensity variation information contained in the captured image to lock-in, identify, and generate a test result. In one exemplary implementation, image data analyzer 210 contains one or more digital filters that isolate one or more spatial frequency components of the periodic pattern. For example, the one or more digital filters are operative to detect the spectral components of a binary pattern associated with a particular lateral-flow strip 100. In this case, the one or more digital filters operate to isolate a spatial frequency component, say, of 5 cycles/cm from the binary pattern.

As a further example, image data analyzer 210 uses a digital image processing technique incorporating a pattern recognition algorithm. The pattern recognition algorithm incorporates frequency lock-in, edge detection, pixel intensity evaluation and other procedures to generate a qualitative pass-fail test result. The test result is coupled via link 207 from image data analyzer 210 to display 215.

Figure 15:
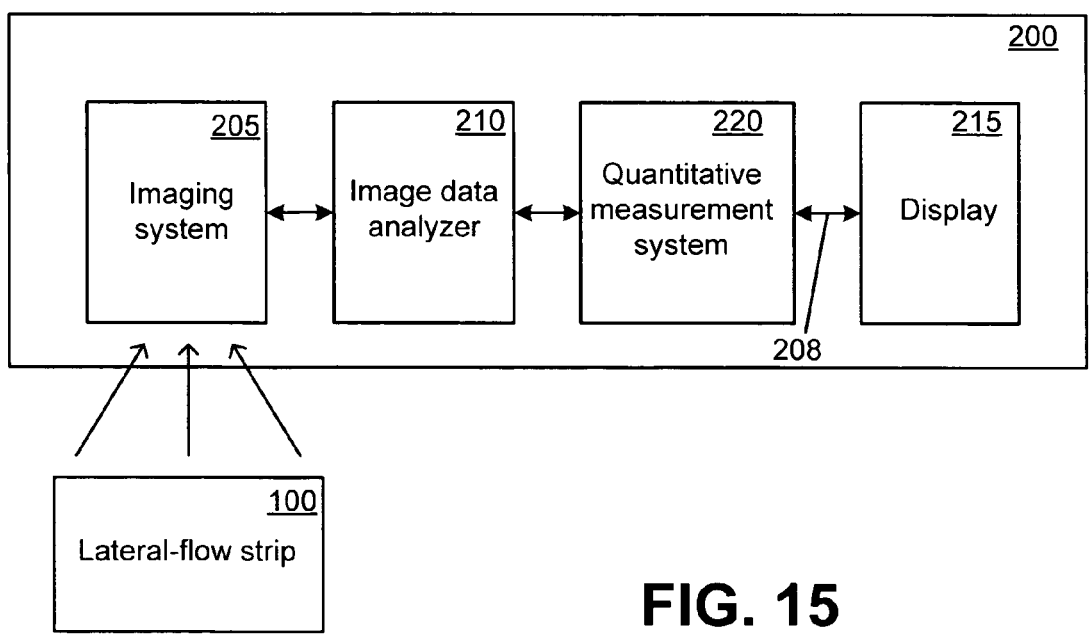
FIG. 15 shows a second exemplary embodiment in accordance with the invention, of a rapid diagnostic test system for obtaining test results from the lateral-flow strip of FIG. 1.

In certain embodiments such as the one shown in FIG. 15, a quantitative measurement system 220 is included so as to obtain a quantitative test result. In one exemplary application, a quantitative test result is obtained from the intensity of the test pattern in the captured image. In another exemplary embodiment, a magnitude of a spatial frequency component is used to obtain a quantitative test result.

Typically, quantitative test results provide greater information than qualitative test results, especially in applications such as cholesterol level testing, alcohol level testing, drug testing, and sugar level testing, to name a few. The test result is coupled via link 208 from quantitative measurement system 220 to display 215 for displaying a simple pass-fail result and/or a quantitative result such as an alcohol level, for example.

Figure 16:
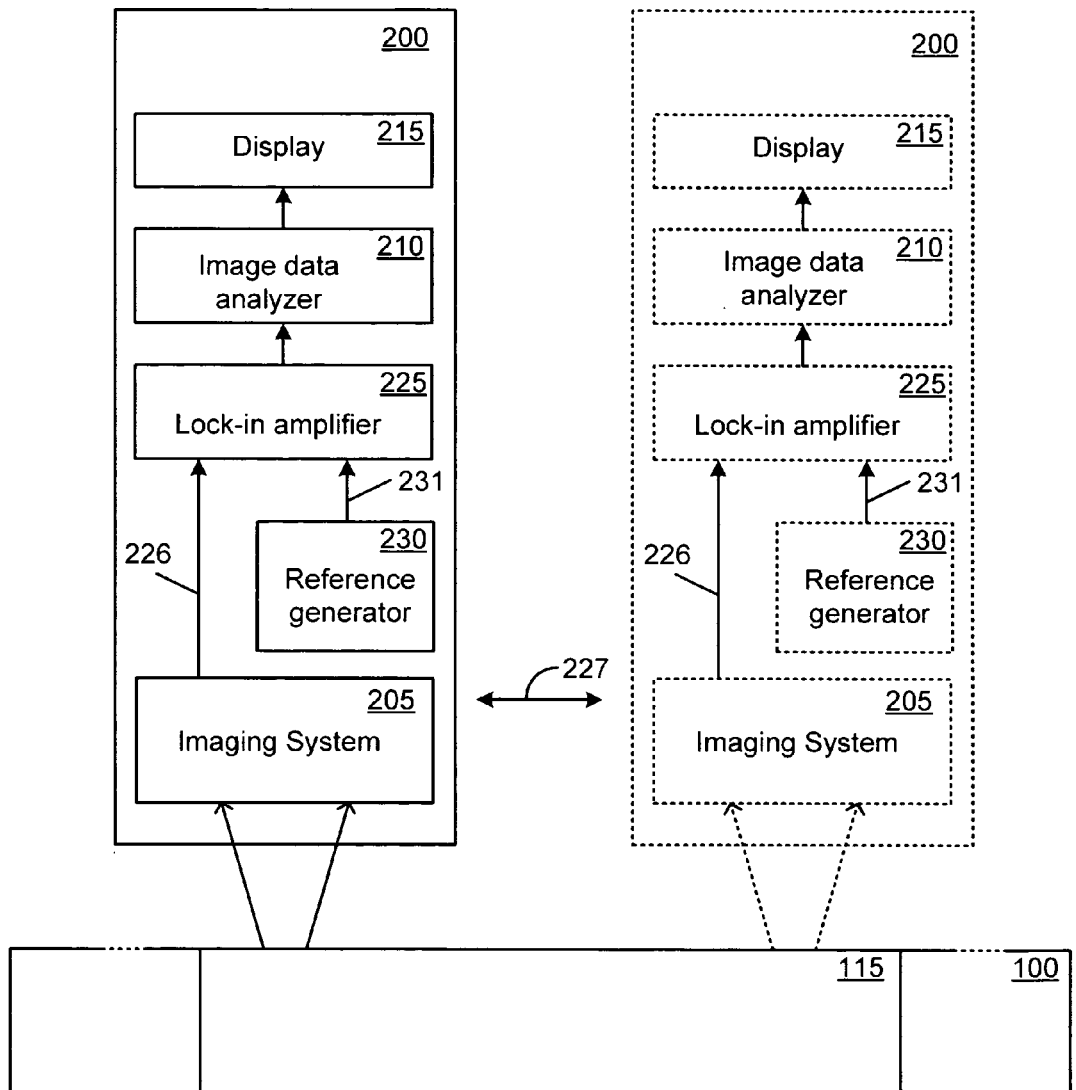
FIG. 16 illustrates a third exemplary embodiment in accordance with the invention, of a rapid diagnostic test system for obtaining test results from the lateral-flow strip of FIG. 1.

FIG. 16 shows a third exemplary embodiment in accordance with the invention, of a rapid diagnostic test system 200 for obtaining test results from the lateral-flow strip 100 described above. In this exemplary embodiment, rapid diagnostic test system 200 is a scanning system such as a hand-held scanner or a desktop scanner, which is operated in a scanning mode to capture a partial or complete image of lateral-flow strip 100. Image capture is assisted by the periodic pattern present in test result region 115. In part, this is carried out by using a lock-in amplifier 225 coupled to image data analyzer 210. The operational aspect of this configuration is described below in further detail.

Rapid diagnostic test system 200 is moved at a constant scan rate in an axial direction corresponding to a longitudinal axis of the periodic pattern. The axial direction is indicated by arrow 227. Imaging system 205 thereby captures a sequence of images and generates a scanned output signal having a temporal frequency (e.g. cycles/sec) that is equal to the product of the actual scan rate (e.g. cm/sec) of rapid diagnostic test system 200 and the spatial frequency (e.g. cycles/cm) of the periodic pattern present in test result region 115. The scanned output signal is provided via link 226 to lock-in amplifier 225.

Lock-in amplifier 225 is further provided via link 231 a reference signal generated by reference signal generator 230. The reference signal is generated by signal generator 230 using a pre-determined, known scan rate of rapid diagnostic test system 200 and a known spatial frequency that corresponds to an expected periodic pattern in lateral-flow strip 100. The temporal frequency of the generated reference signal is equal to the product of the known scan rate of rapid diagnostic test system 200 and the spatial frequency of the expected periodic pattern of lateral-flow strip 100. Lock-in amplifier 225 uses the reference signal together with the scanned output signal to generate one or more signals that are further used in image data analyzer 210 to generate qualitative and/or quantitative test results that are displayed via display 215.

In lieu of, or in addition to, scanning in the direction indicated by arrow 227, rapid diagnostic test system 200 may be moved at a constant scan rate in an axial direction that is opposite to that indicated by arrow 227 and/or bi-directionally.

Figure 17:
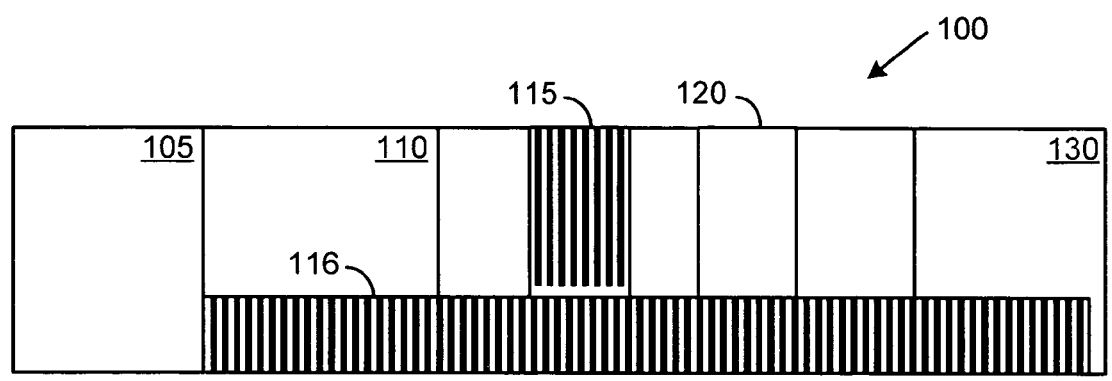
FIG. 17 shows an exemplary reference periodic pattern provided on the lateral-flow strip in accordance with the invention.

FIG. 17 shows a reference periodic pattern 116 that is provided on lateral-flow strip 100. In this exemplary embodiment, the reference periodic pattern 116 extends along the length of lateral-flow strip 100 and straddles multiple regions. In other embodiments, reference periodic pattern 116 may be implemented in various other ways. For example, in another embodiment, the reference periodic pattern 116 is located solely inside test completion region 120. In yet another exemplary embodiment, reference periodic pattern 116 is located inside test result region 115 parallel to the periodic pattern used for detection.

Reference periodic pattern 116 may be used for a variety of purposes. For example, in a first instance, reference periodic pattern 116 provides a priori information used for detecting the periodic pattern of the test. In this case, reference periodic pattern 116 is typically a replica of the periodic pattern used for testing.

For example, this may be carried out using an alternative embodiment of the rapid diagnostic test system 200 of FIG. 16. In this embodiment, reference generator 230 is omitted and rapid diagnostic test system 200 instead employs two scanner heads one of which is used to generate the reference periodic pattern. The first scanner head is configured to scan the reference periodic pattern, which is always present in lateral-flow strip 100 after completion of a test. The second scanner head is configured to scan the periodic pattern, which may or may not be present depending if the test result is positive or negative respectively. The output of the first scanner head is used to generate the reference signal for the lock-in amplifier and the output of the second scanner head is used as the input signal to the lock-in amplifier described above.

Figure 18:
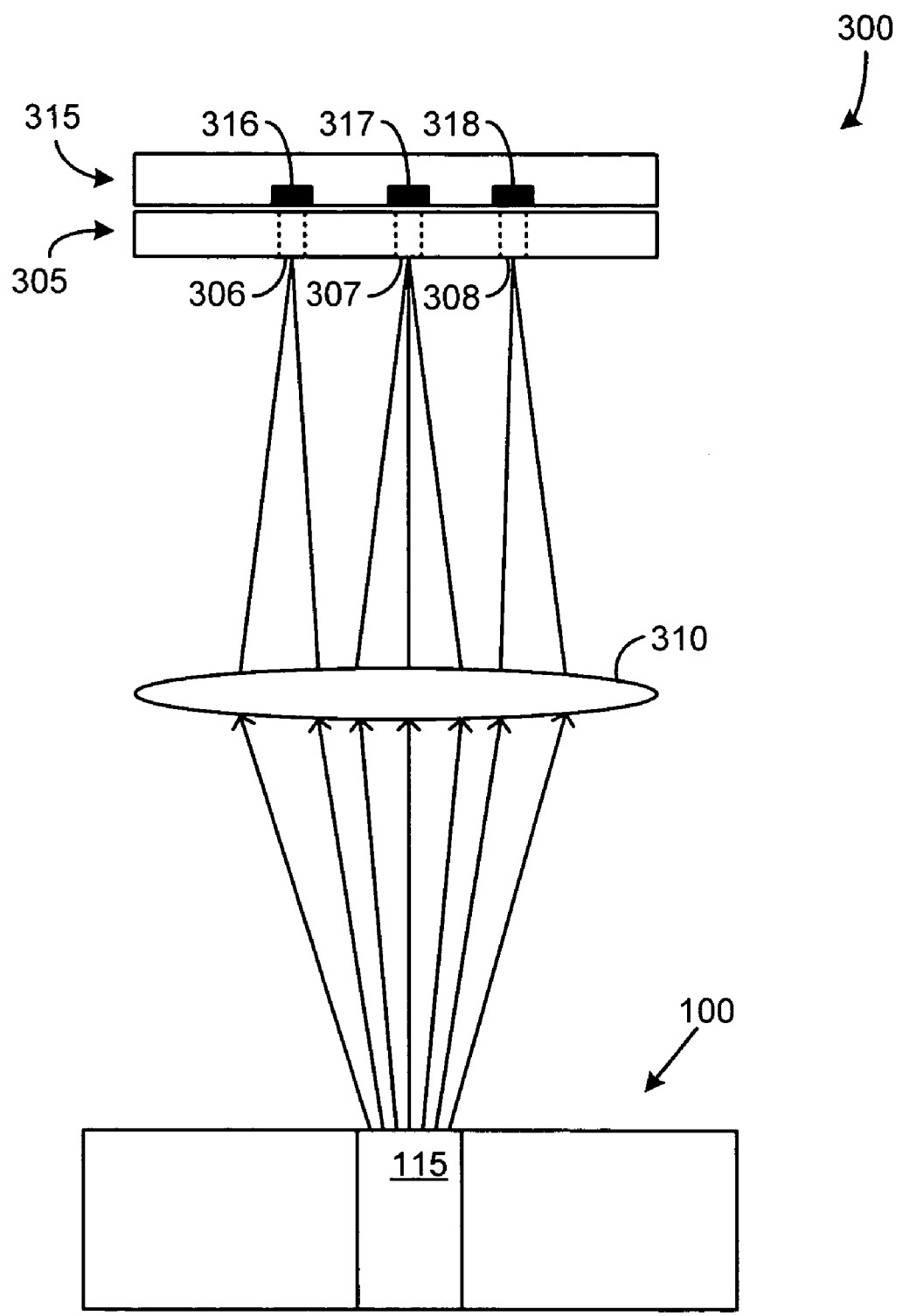
FIG. 18 shows a fourth exemplary embodiment in accordance with the invention, of a rapid diagnostic test system for obtaining test results from the lateral-flow strip of FIG. 1.

FIG. 18 shows a fourth exemplary embodiment in accordance with the invention, of a rapid diagnostic test system 300 for obtaining test results from the lateral-flow strip 100. In this embodiment, an optical lens 310 is used to obtain a Fourier transformed image of at least a portion of lateral-flow strip 100. Optical lens 310 is positioned with reference to lateral-flow strip 100 so as to project a Fourier transformed image upon a mask 305. In this example, an image of test result region 115 is projected via optical lens 310 onto mask 305. Mask 305 contains apertures at locations corresponding to Fourier components of interest in the projected image. Three exemplary apertures 306, 307, and 308 are shown. The image is passed through mask 305 and on to an optical detector 315, which contains detector elements. Three exemplary detector elements 316, 317, and 318 are shown. The signals generated by the detector elements are provided to an image data analyzer (not shown), such as image data analyzer 210, for image analysis and subsequent display of test results.

Figure 19:
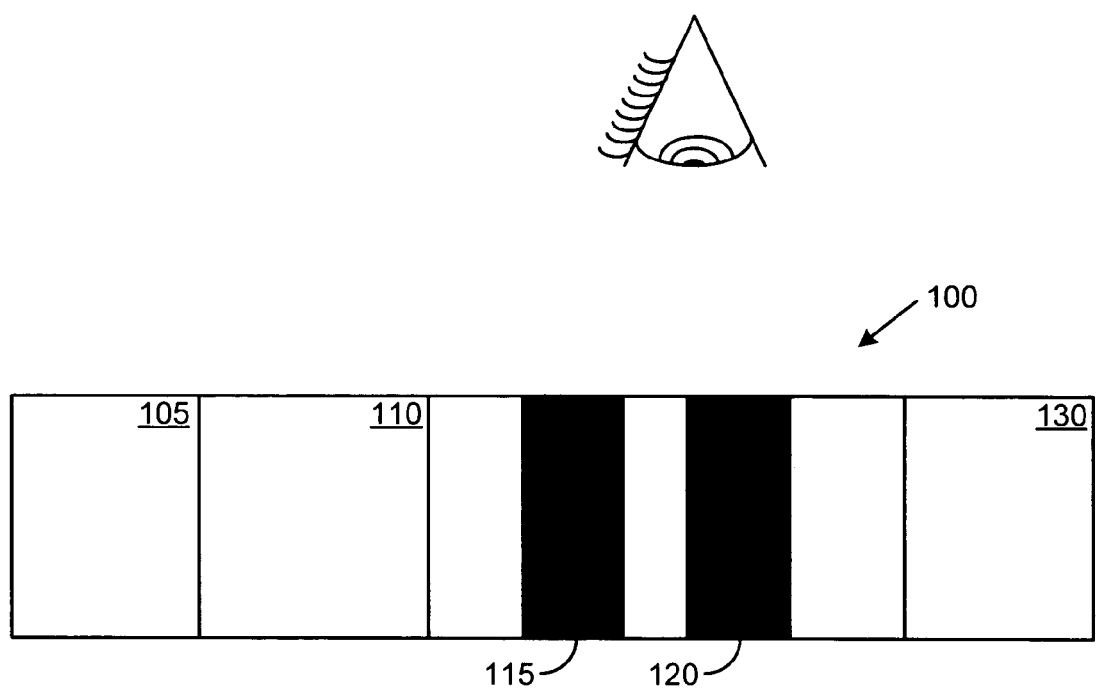
FIG. 19 shows a manual process in accordance with the invention, for obtaining test results from the lateral-flow strip of FIG. 1.

In contrast to the automatic detection systems described above, FIG. 19 shows a manual process for obtaining test results from lateral-flow strip 100. In this process, an operator visually inspects lateral-flow strip 100 and interprets his observation to obtain a test result. For example, a positive test result is qualitatively indicated when the periodic pattern is visible with a certain coloration. Furthermore, the intensity of the visible periodic pattern provides a quantitative test result.

Figure 20:
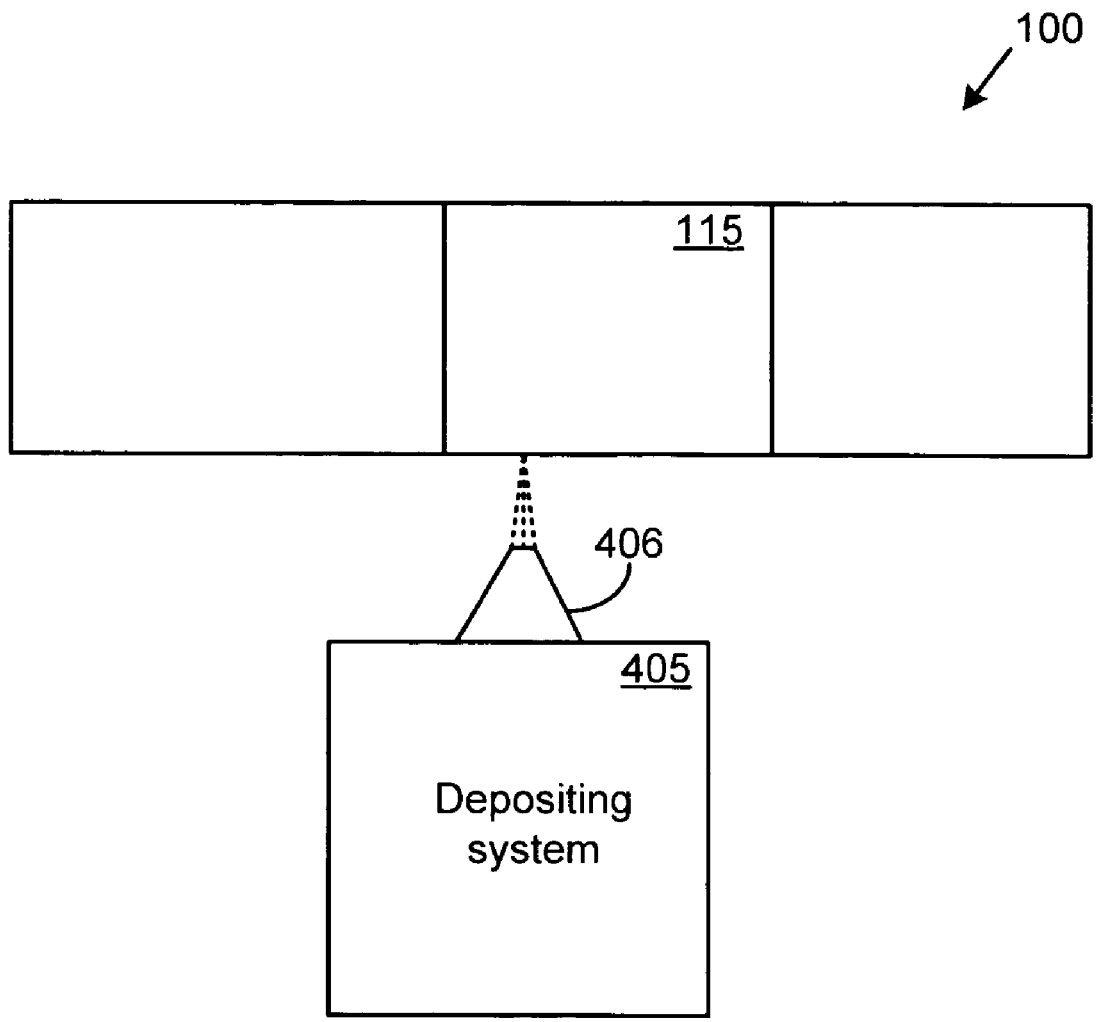
FIG. 20 shows an exemplary embodiment in accordance with the invention, of a deposition system for depositing a substance upon the lateral-flow strip of FIG. 1.

FIG. 20 shows an exemplary embodiment in accordance with the invention, of a deposition system 405 for depositing a substance upon at least a portion of lateral-flow strip 100. In one exemplary embodiment, deposition system 405 is used to deposit a binding agent in a periodic pattern upon test result region 115. Deposition system 405, which incorporates ink-jet printer technology, includes a nozzle 406 to direct the binding agent as a directional jet towards lateral-flow strip 100. Deposition system 405 may be used to deposit a binding agent on various areas of lateral-flow strip 100 in addition to test result region 115 shown in FIG. 20.

Figure 21:
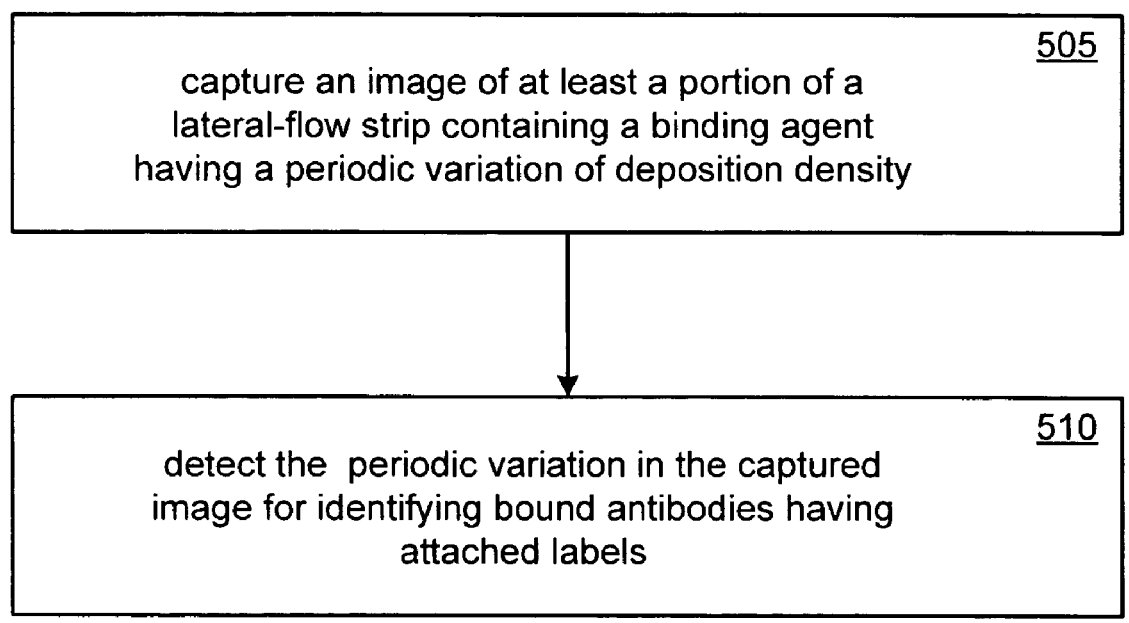
FIG. 21 shows a flowchart of a rapid diagnostic testing method in accordance with the invention.

FIG. 21 shows a flowchart of a rapid diagnostic testing method. In block 505, an image of at least a portion of a lateral-flow strip is captured. The lateral-flow strip contains a binding agent with a periodic variation in deposition density as described above. In block 510, the periodic variation is detected in the captured image in order to identify the presence of, and optionally quantify, bound antibodies with attached labels. The presence of bound antibodies with attached labels is indicative of a positive test result, while a negative test result is indicated by the lack of bound antibodies with attached labels.

The above-described embodiments are merely set forth for a clear understanding of the principles of the disclosure. Many variations and modifications may be made without departing substantially from the disclosure. All such modifications and variations are included herein within the scope of this disclosure.

I claim:

1. A rapid diagnostic test system comprising:
    a lateral-flow strip for performing a binding assay, the lateral-flow strip comprising a binding agent with a deposition density that varies periodically along at least a portion of the lateral-flow strip; and
    an imaging system operative to capture an image of the portion of the lateral-flow strip, wherein the imaging system comprises a lens configured to collect light from the portion of the lateral-flow strip and generate by free-space propagation, a Fourier transformed image of at least a portion of the lateral-flow strip.

2. The system of claim 1, further comprising:
    an image data analyzer coupled to the imaging system, the image data analyzer operative to use a priori information of the deposition density to analyze the captured image for detecting a bound antibody having a label attached thereto.

3. The system of claim 2, wherein the imaging system is a digital image capture system operative to generate digital image data.

4. The system of claim 1, wherein the binding agent is a bound antibody and the deposition density varies periodically in one of a sinusoidal pattern and a binary pattern and wherein the system further comprises an optical detector configured to detect the one of a sinusoidal pattern and a binary pattern from the Fourier transformed image.

5. The system of claim 1, wherein the binding agent is a bound antibody and the deposition density varies periodically in one of a sinusoidal pattern and a binary pattern.

6. The system of claim 5, further comprising:
an image data analyzer coupled to the imaging system, the image data analyzer operative to use a priori information of the one of a sinusoidal pattern and a binary pattern to analyze the captured image for detecting a bound antibody having a label attached thereto.

7. The system of claim 6, further comprising:
a deposition system comprising a nozzle configured to direct the bound antibody towards the portion of the lateral-flow strip.

8. The system of claim 6, further comprising:
an image data analyzer coupled to the imaging system, the image data analyzer operative to analyze the captured image comprising the one of a sinusoidal pattern and a binary pattern for detecting a bound antibody having a label attached thereto.

9. The system of claim 8, wherein the lateral-flow strip further comprises a reference imaging pattern for enabling the image data analyzer to detect the one of the sinusoidal pattern and a binary pattern.

10. A rapid diagnostic testing method, the method comprising:
contacting a lateral-flow strip with a test sample comprising at least one target anayte;
labeling the target analyte to generate a labeled target anayte;
binding the labeled target analyte to a binding agent having a periodic variation of deposition density;
capturing an image of at least a portion of the lateral-flow strip; and
detecting the periodic variation in the captured image to identify bound labeled target analyte.

11. The method of claim 10, wherein capturing the image comprises using a digital image capture system to generate digital image data.

12. The method of claim 11, wherein detecting the periodic variation comprises one of a) visual detection by a human operator and b) automatic detection.

13. The method of claim 11, wherein detecting the periodic variation comprises detecting a reference imaging pattern on the lateral-flow strip.

14. The method of claim 10, wherein capturing the image comprises a Fourier-transformation by propagating light through a lens.

15. The method of claim 10, wherein capturing the image comprises:
scanning the lateral-flow strip at a first scan rate;
generating a scanned output signal having a temporal frequency equal to a product of the first scan rate and a spatial frequency of the periodic variation of deposition density.

16. The method of claim 10, wherein detecting the periodic variation comprises identifying a spatial frequency component in the captured image.

17. The method of claim 16, further comprising using a change in a magnitude of the spatial frequency component to generate a quantitative test result.

18. A lateral-flow test strip, comprising:
a test result region comprising a binding agent having a periodic variation of deposition density, wherein the periodic variation comprises one of a sinusoidal pattern and a binary pattern; and
a test completion region comprising the binding agent.

19. The lateral-flow test strip of claim 18, further comprising a reference periodic pattern.

20. The lateral-flow test strip of claim 18, wherein the reference periodic pattern is located in the test completion region.

* * * * *